United States Patent [19]

Medway

[11] Patent Number: 4,929,237
[45] Date of Patent: May 29, 1990

[54] HYPODERMIC NEEDLE PROTECTION DEVICE

[76] Inventor: David Medway, 2401 H St., NW. #805, Washington, D.C. 20037

[21] Appl. No.: 268,242

[22] Filed: Nov. 7, 1988

[51] Int. Cl.⁵ ............................................. A61M 5/32
[52] U.S. Cl. .................................... 604/198; 128/763
[58] Field of Search ...................... 128/763, 765, 770; 604/110, 157, 192, 194, 197, 198, 263

[56] References Cited

U.S. PATENT DOCUMENTS

| | | | |
|---|---|---|---|
| 1,921,034 | 8/1933 | Marche | 604/197 |
| 2,876,770 | 3/1959 | Whik | 604/201 |
| 3,368,558 | 2/1968 | Sarnoff et al. | 604/198 |
| 4,316,473 | 2/1982 | Beskin | 128/763 |
| 4,659,330 | 4/1987 | Nelson et al. | 604/263 |
| 4,664,654 | 5/1987 | Strauss | 604/198 |
| 4,758,231 | 7/1988 | Haber et al. | 128/763 |
| 4,801,295 | 1/1989 | Spencer | 604/263 |

Primary Examiner—Max Hindenburg
Attorney, Agent, or Firm—Sherman Parrett

[57] ABSTRACT

A safety device for preventing contact with exposed contaminated hypodermic needles includes a housing unit, syringe, hypodermic needle, spring for retracting the hypodermic needle and safety elements to prevent accidental removal of the syringe from the housing unit and exposure of the needle.

13 Claims, 2 Drawing Sheets

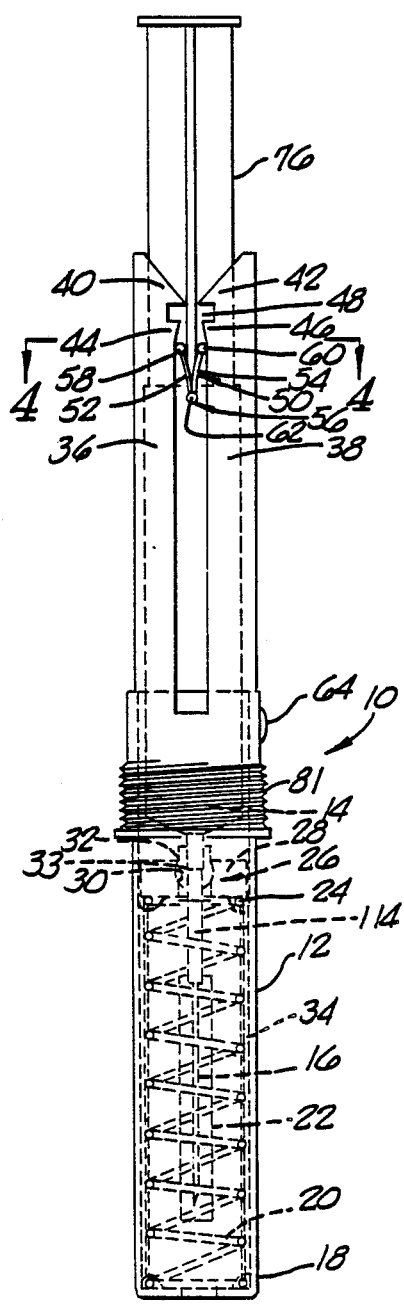
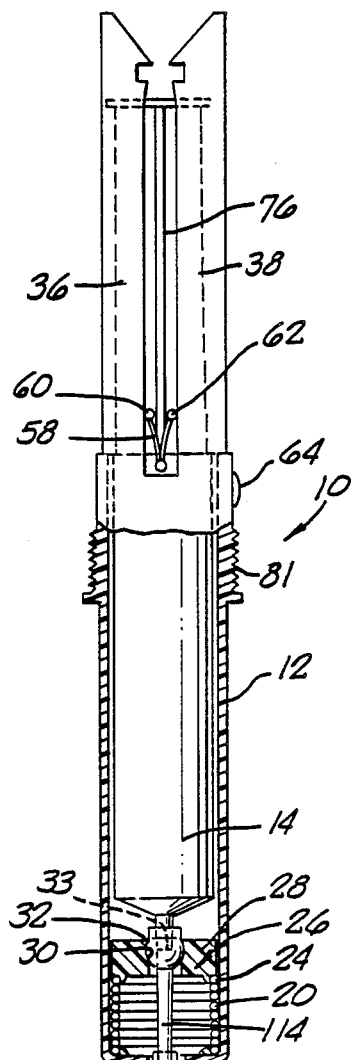
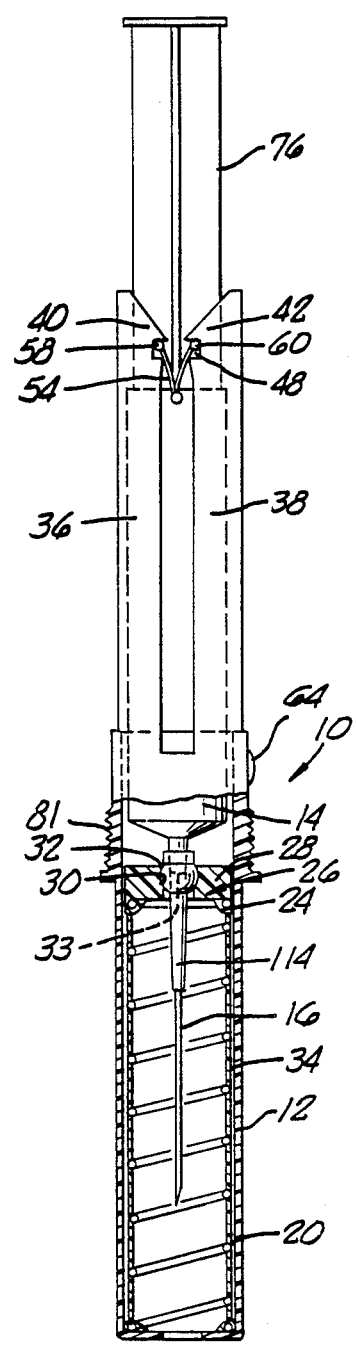
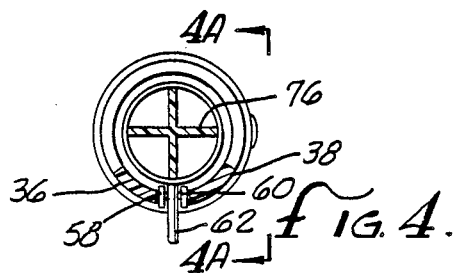
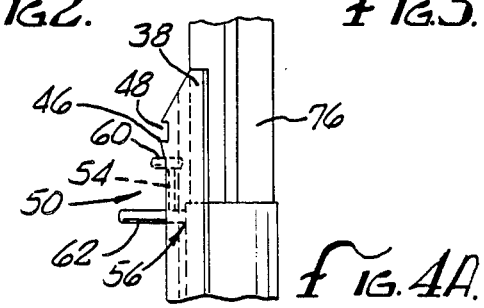

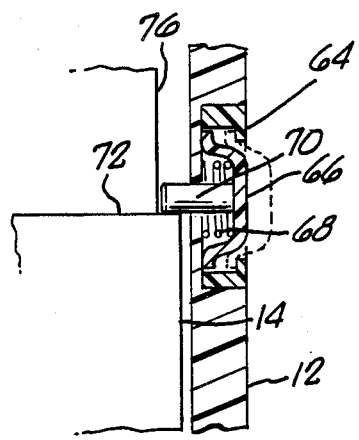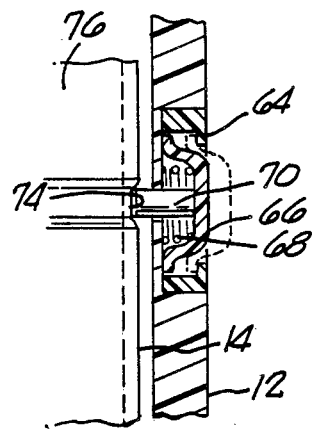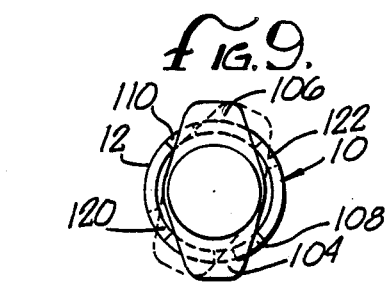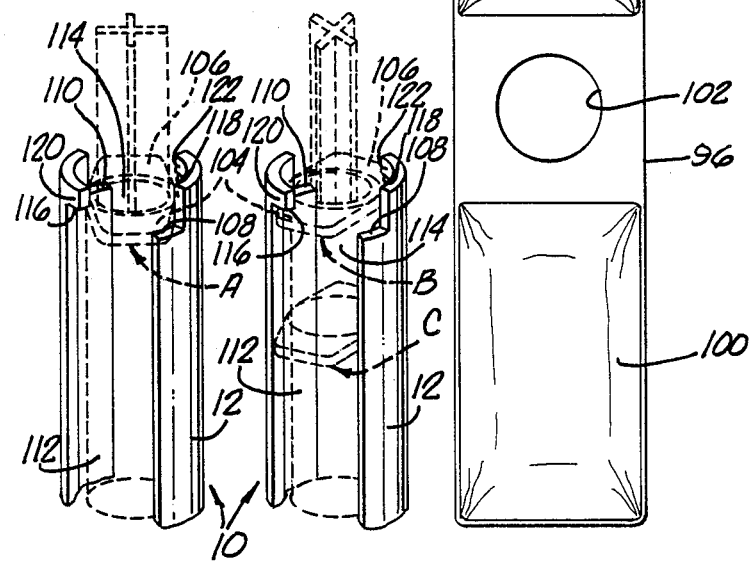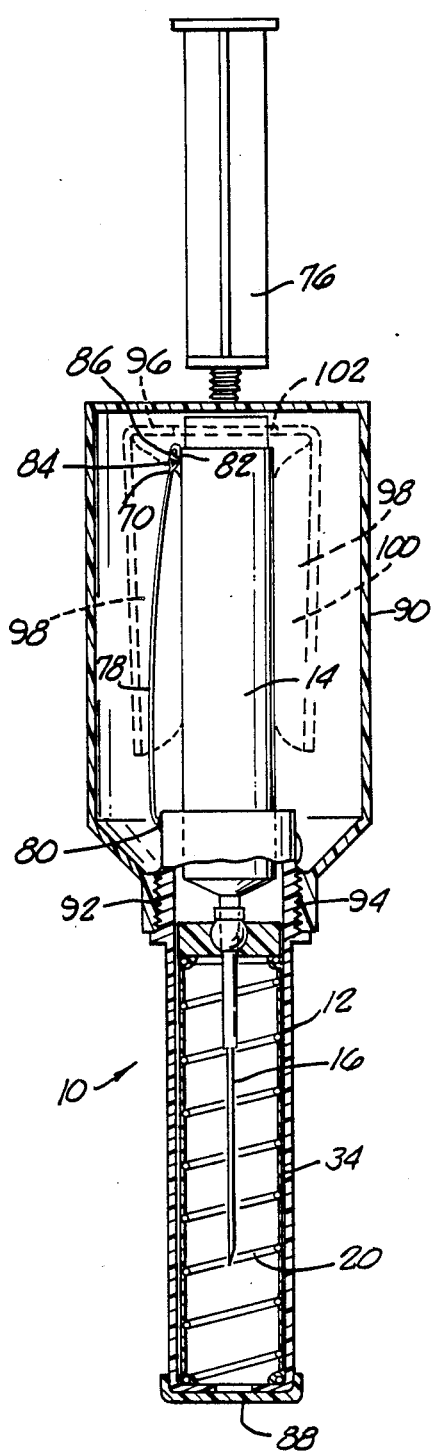

HYPODERMIC NEEDLE PROTECTION DEVICE

FIELD OF THE INVENTION

This invention relates to hypodermic syringes and more particularly to a safety device to protect users of hypodermic syringe needles from inadvertent punctures from contaminated needles.

BACKGROUND OF THE INVENTION

Contaminated hypodermic needles present a hazard to health care personnel who may be inadvertently stuck by a needle in the course of or following routine medical procedures, such as blood drawings and injections. It has been reported that at least ten percent of health-care personnel are injured annually by needles and this estimate may be low based on a higher number of personnel who fail to report incidents of needle sticks. A number of infectious agents may be transmitted by contact with contaminated needles including non A-non B hepatitis, hepatitis B and human immunodeficiency virus (HIV). (Bonnett, J. Practical Nursing, pp. 33-35, June 1988). In particular, the transmission of fatal diseases such as Acquired Immune Deficiency Syndrome ("AIDS") to health care personnel has been demonstrated from accidental contact with contaminated needles, and poses a significant threat to such individuals.

Hypodermic needles are typically exposed for a certain period of time after use. During the time period in which the contaminated needle is exposed, individuals are susceptible to contact with and possible infection from the needle. Disposal of contaminated needles occurs by various procedures including recapping the needle and then disposing of the capped needle; cutting off the end of the needle, or disposal of the needle and syringe as a unit.

Various devices have been used in the past to cover hypodermic needles. These devices include those designed to hide the hypodermic syringe needle from view of the patient and/or to advance a needle into the patient's body or to administer preselected or multiple doses of medicament to the patient. For example, U.S. Pat. No. 2,876,770 describes a device for a hypodermic syringe for hiding the syringe needle from view of the patient. The device includes a sheath and a coil spring surrounding the hypodermic needle. The sheath is retracted as the needle is pushed into the patient's skin and since the sheath moves freely, the needle may be unintentionally exposed. U.S. Pat. No. 1,921,034 describes a carrying device for a syringe and employs a spring to advance the needle from the case a predetermined depth into the patient's skin. The device also contains a saturating material for sterilizing the needle before insertion into tissue. The sterilizing material seals the container after retraction of the needle. The syringe needle must be manually retracted into the case after use and may also be unintentionally exposed. U.S. Pat. No. 4,573,976 provides an injection apparatus having a needle guard which when extended obstructs access to the point of the needle and may be retracted to expose the needle. The extension and retraction of the needle is accomplished by interlocking units which are manually slid against one another to move a syringe carrying the needle. U.S. Pat. No. 4,664,653 describes a manually operated injection apparatus which is capable of administering repeated doses of a drug. U.S. Pat. No. 4,664,654 describes a hypodermic needle guard which includes a sliding member and a spring surrounding a needle. The sliding member may be retracted and locked into a retracted position to reveal the needle. The sliding member may be locked in position to expose the needle a certain amount and is unlocked by advancing the needle further into a patient. When the needle is withdrawn the guard may be locked into place to cover the needle; however, the guard may not be put into operation, such that the needle remains exposed. U.S Pat. No. 4,675,005 describes a retractable disposable syringe for manually retracting a needle into a syringe.

The aforementioned devices are intended for injection of medicaments into a subject. The devices may retain the needle in an exposed position during or after use allowing inadvertent puncture of the operator. There remains a need for a syringe device for injecting medicaments and/or withdrawing body fluids from a patient, and which eliminates exposure of an operator to a contaminated needle, to reduce the risk of contracting AIDS and other infectious diseases from inadvertent contact with the needle.

SUMMARY OF THE INVENTION

The invention is a device for preventing exposure of a contaminated hypodermic needle comprising:

(a) a housing unit having a larger proximal and smaller distal aperture, for receiving a syringe and hypodermic needle attached to said syringe;

(b) a syringe operatively engageable within and removable from said housing unit comprising a syringe chamber for containing liquid medicament or body fluid and a hypodermic needle having a base, said needle operatively engageable with and removable from said syringe;

(c) spring means attached at the distal end of said housing unit, said spring means engaging the base of said hypodermic needle, such that a pushing force applied to the proximal end of said syringe moves said syringe distally within said housing unit;

whereby, when said pushing force is released said syringe retracts proximally within said housing unit, retracting said hypodermic needle within said housing unit to prevent contact of said hypodermic needle with the operator of said device.

BRIEF DESCRIPTION OF THE DRAWINGS

FIG. 1 is a side elevation of the invention including a syringe and capped needle;

FIG. 2 is a partial cross section of the invention and depicts the syringe and capped needle inserted fully into the distal end of the invention such that the spring is fully compressed;

FIG. 3 is a partial cross section of the invention and depicts the syringe located at the proximal end of the invention with the spring in an extended position;

FIG. 4 is a cross section taken along line 4—4 of FIG. 1;

FIG. 4A is a side view taken along line 4A—4A of FIG. 4;

FIG. 5 is a partial enlarged cross section of the button;

FIG. 6 is an alternative embodiment of FIG. 5;

FIG. 7 is a cross section of the invention depicting an alternative embodiment of the means for securing the syringe and depicting a detachable plunger and a cover for the syringe;

FIG. 8 is a plan view of an insulating jacket;

FIG. 9 is a top plan view of a syringe inserted into an alternative embodiment of the invention shown in FIG. 10, infra;

FIG. 10A is a perspective view of an alternative embodiment of the invention; and FIG. 10B is a perspective view of an alternative embodiment of the invention.

DETAILED DESCRIPTION OF THE INVENTION

Referring now to FIG. 1, there is shown generally at 10 a disposable container of the present invention which comprises a cylindrical housing unit 12 for receiving a syringe body 14 and hypodermic needle 16. The housing unit 12 and syringe body 14 may be manufactured from a transparent or substantially transparent material so that fluids contained within the syringe body 14 may be visualized. At the distal end 18 of the housing unit 12 a coil spring 20 is located and may be attached at its base to the housing unit 12 as shown in FIG. 1. The spring 20 may be encased within a thin, flexible material such as a rubber or plastic material. The spring 20 encircles the hypodermic needle 16 which may have a cap 22, when the needle 16 attached to the syringe body 14 is inserted into the housing unit 12. In a preferred embodiment, the proximal end 24 of the spring 20 is attached to a locking element shown generally at 26 consisting of a block 28, containing a pocket 30 with flanges 32 for securely grasping the base 33 of the hypodermic needle 16 when the syringe body 14 is inserted into the housing unit 12. The locking element 26 will prevent accidental removal of the needle 16 from the housing unit 12. A flexible, collapsible sleeve 34, for example made of clear plastic such as "shrink-wrap", may be used to provide added strength to the spring, to provide additional resistance to accidental removal of the needle 16 from the housing unit 12 and to help prevent leakage of fluid from the container.

Referring to FIGS. 1-3, the housing unit 12 includes approximately parallel tracks 36 and 38 for providing a pathway of insertion of the syringe into the housing unit 12, and for preventing accidental backwards ejection of the syringe and hypodermic needle from the container 10 during or after use. Tracks 36 and 38 have sloping terminii 40 and 42, and protruding edges 44 and 46. The track terminii and protruding edges together define a notch 48. As seen in FIG. 1, the syringe body 14 also contains a safety catch shown generally at 50 having arms 52 and 54. The safety catch 50 is attached to the syringe body 14 at the base 56 of the catch 50. The arms extend upwardly at an angle of up to 90° from the surface of the syringe body. The safety catch 50 also includes shafts 58, 60 and 62. The shafts 58, 60 and 62, extend perpendicularly from the arms 52 and 54 and base 56 of the catch 50. In operation, catch arms 52 and 54 are pressed inwardly by terminii 40 and 42 as the syringe body 14 is inserted into the pathway defined by the tracks 36 and 38. As the syringe is manually advanced to expose the needle 16 for insertion into the patient, spring 20 is compressed and safety catch arms 52 and 54 are moved past the terminii 40 and 42, through the notch 48 and past protruding edges 44 and 46 by the operator squeezing together arms 52 and 54 by pressing shafts 58 and 60 inwards. Upon exiting protruding edges 44 and 46, the catch arms 52 and 54 expand outwardly as shown in FIGS. 1 and 2. If the operator should accidentally release his/her hold on the syringe and container, or should the entire device be dropped, the syringe body 14 will automatically be advanced proximally along tracks 36 and 38 as the spring 20 extends, but the syringe will be prevented from further movement when shafts 58 and 60 lodge in the notch 48 and abut against track terminii 40 and 42. The hypodermic needle 16 will then be secured within the container 10 without risk of contact between the contaminated needle and persons in the vicinity of the device. In addition, the locking element 26 will retain the hypodermic needle 16 within the container 10 should the syringe body 14 become detached from the needle 16.

The safety catch 50 may be constructed of a sturdy plastic, rubber or flexible metallic material. The shafts 58, 60 and 62 may also be used to manually advance the syringe into the housing unit 12. For example, the operator may press a finger against shaft 62 once the safety catch 50 passes protruding edges 44 and 46 to continue advancing the syringe into the housing unit 12.

The syringe body 14 is retained in position during injection or withdrawal of body fluid by means of pressure against the housing unit 12 and the syringe body 14. Thus, the walls of housing unit 12 should be resilient to permit application of pressure against the syringe body 14. In a preferred embodiment, the syringe body 14 is locked in position during injection into or withdrawal of fluids from a patient by pressing on button 64. As shown in detail in FIG. 5, button 64 includes a pad 66, a spring 68 and a pin 70. When the pad 66 is depressed by the operator, for example by using his/her thumb, the spring 68 is compressed and pushes pin 70 into the inside of the housing unit 12. When the syringe body 14 is correctly positioned in the device, the pin 70 will prevent further backward movement of the syringe body 14 from the container 10 by contacting the end 72 of the syringe body 14.

In an alternative embodiment, as shown in FIG. 6, movement of the syringe body 14 within the housing unit 12 may be prevented by use of the above described button 64 and an indentation 74 on the surface of the syringe body 14. When the syringe body 14 and hypodermic needle 16 are fully inserted within the container 10, and the button pad 66 is depressed by the operator, the pin 70 will be inserted into the indentation 74 and will prevent further movement of the syringe body 14 until the button is released.

During operation of the syringe and container 10, for an injection of drug or withdrawal of body fluid, the syringe body 14 is preferably fitted with a hypodermic needle 16 having a cap 22. The syringe and capped needle 16 are manually advanced into the housing unit 12 by compressing the coil spring 20 until the capped needle 16 extends beyond the housing unit 12 as shown in FIG. 2. The operator then removes the cap 22 with one hand while holding the syringe and needle in place within the housing unit 12 by pressing button 64. The operator can then penetrate the skin of a patient to give an injection or withdraw a sample of body fluid. The operator's free hand is used to push down against a plunger 76 in the syringe body 14 for an injection or to pull on the plunger 76 to collect the fluid sample. When the injection or fluid withdrawal is complete the operator releases pressure on button 64 causing the now-contaminated hypodermic needle 16 to be retracted into the housing unit 12, by extension of the spring 20. As the spring 20 extends, withdrawing the syringe and needle 16 proximally back through the housing unit 12, the safety catch 50 prevents the syringe from ejecting backward out of the container 10 so as to expose the contaminated needle 16 outside of the container. The plunger 76 may be detachable as shown in FIG. 7.

Alternatively, instead of the safety catch described above, a tether 78, as depicted in FIG. 7, may be used in the invention. The tether 78 may consist of a length of plastic, rubber or other slightly flexible material which is attached at one end 80 to the housing unit 12 and at the other end 82 to the syringe body 14. For example, the tether 78 may have a small loop 84 at the end for attaching to the syringe body 14, and the loop 84 may be slid over a small hook 86 constructed in the syringe body 14. Other methods for attaching a tether 78 to the syringe are contemplated, including permanent (continuous) attachment. The tether should be short enough to prevent exit of the tip portion of the hypodermic needle 16 from the housing unit 12 such that the tip of a contaminated needle would be exposed at any time outside the container.

The housing unit 12 may also be fitted with a seal 88 as shown in FIG. 7. The syringe and contaminated needle may be disposed after use by retracting the syringe and needle into the container and covering the base of the container 10 with the seal 88 and disposing of the entire sealed container. However, if the device is used to withdraw a sample of body fluid which must be kept insulated i.e. to at a particular temperature, for example blood from a patient, then the housing unit 12 may be closed off both by the seal 88 and by placing an outer cover 90 such as depicted in FIG. 7, around the portion of the syringe body 14 that extends from the housing unit 12. The outer cover 90 may be attached to the housing unit 12 by grooves 92 on the cover 90 and threads 94 on the housing unit 12. The cover 90 is then rotated around the threads 94 on the housing unit 12. In this manner, packing or insulating material such as ice may be added inside the cover 90 to insulate fluid in the syringe body 14 when the cover is in place.

The outer cover 90 thus permits transfer and temporary storage of any fluids contained within the syringe body 14 without requiring removal of the syringe body 14 from the container 10 and thus exposure of the contaminated needle 16 outside the container 10. Alternatively, an insulating jacket 96 as depicted in FIG. 8 consisting of pouches 98 and 100 and aperture 102 could be placed over the syringe body 14, preferably with the plunger 76 detached as shown in FIG. 7 so as to reduce the overall size of the container. The pouches 98 and 100 can then contact and insulate fluids in the syringe body 14. The cover 90 may then be screwed around the syringe body 14 containing the sample and encased by the insulating jacket 96.

If desired, the syringe body 14 may be removed from the container 10 at any time by pressing safety catch arms 52 and 54 together to release them from the tracks 36 and 38 or, if a detachable tether 78 is used, by releasing the tether 78 from the syringe body 14. If the syringe is removed, the contaminated needle 16 will normally be retained in the locking element 26 and remain in the container 10. The entire container 10 containing the contaminated needle 16 in the locking element 26 may then be disposed.

In an alternative embodiment depicted in FIGS. 9 and 10A and 10B, a syringe having opposing upper and lower lips 104 and 106 may be used with a modified container 10 to provide a non-linear pathway for syringe movement into housing unit 12 as depicted in FIGS. 10A and 10B. In this embodiment, the walls of the housing unit 12 are cut away to provide opposing upper and lower non-linear pathways for movement of lips 104 and 106 distally into the container as shown in FIG. 10A and 10B. In operation, the syringe is inserted into the top of the housing unit, such that the lips 104 and 106 are positioned vertically as shown in FIG. 10A. In this position (A in FIG. 10A), the lips 104 and 106 rest on the surfaces of ridges 108 and 110 and further movement distally into the container is prevented. The operator than manually adjusts the syringe, rotating it such that the lips 104 and 106 are positioned within the channels 112 and 114 (position B in FIG. 10B). In this position, the syringe may be manually moved distally into the housing unit (position C in FIG. 10B) using a pushing force to compress the spring and advance the syringe needle as described above. The syringe may be held in position within the container and/or upon insertion of the needle into a patient using the button mechanism described above. If the syringe is unintentionally released, ejection from the container is prevented by abutment of the lips 104 and 106 against the inner surfaces 116 and 118 of struts 120 and 122. If desired, the syringe may be removed from the container by rotating the syringe such that the lips 104 and 106 are once again in position A (FIG. 10A) and pulling the syringe out from the housing unit 12.

It will be appreciated that the apparatus may be used with any syringe and needle arrangement, including commercially available hypodermic syringes and needles. The syringe body for use in the container 10 preferably may consist of a hypodermic syringe modified to have a safety catch 50 such as that shown in FIGS. 1–3 for insertion into the tracks 36 and 38 to prevent accidental dislocation of the syringe from the container. In addition, the hypodermic needle may require a modified base 33 as shown in FIGS. 1–3 for insertion into the locking element 26, and an extended neck 124. If it is desired to employ a vacuum pressure tube with a two-ended needle and its holder (e.g. a Vacutainer brand system, available from Becton Dickinson, Co., Rutherford, N.J.) for withdrawal of blood samples from patients, then the needle holder should be modified to have a projection or a tether system as described above and a standard vacuum tube can then be used. Once the needle-holder has been advanced distally and the needle extending from the housing unit 12 has been inserted into the patient, the operator merely pushes the vacuum tube into the needle extending from the opposite end of the needle that penetrates the skin of the patient, compressing the spring as described above, to withdraw blood or other fluid.

The present invention thus prevents contact with a contaminated hypodermic needle during and after use by permitting automatic retraction and shielding of a contaminated needle. If the device is dropped, the hypodermic needle will be automatically retracted back into the container to prevent unintentional needle sticks.

As will be apparent to those skilled in the art in which the invention is addressed, the present invention may be embodied in forms other than those specifically disclosed herein without departing from the spirit or essential characteristics of the invention. Particular embodiments of the present invention described above are therefore to be considered in all respects as illustrative and not restrictive. The scope of the present invention is as set forth in the appended claims rather than being limited to the examples contained in the foregoing description.

I claim:

1. A device for preventing exposure of a contaminated hypodermic needle comprising:
   a housing unit having a larger proximal and smaller distal aperture for receiving a syringe and hypodermic needle attached to said syringe;
   a syringe operatively engageable within and removable from said housing unit comprising a syringe chamber for containing liquid medicament or body fluid and a hypodermic needle having a base, said needle operatively engageable with and removable from said syringe;
   spring means positioned at the distal end of said housing unit, said spring means engaging the base of said hypodermic needle, such that a pushing force applied to the proximal end of said syringe compresses said spring means and moves said syringe distally within said housing unit;
   safety catch means for retaining said housing unit and syringe in engaged relationship in the absence of any pushing or retaining force applied to said syringe; and
   locking means for selectively preventing relative movement between said housing and syringe and hypodermic needle when the hypodermic needle is in use with the spring means compressed,
   whereby, when said pushing force is released said spring means extends and said syringe retracts proximally within said housing unit, retracting said hypodermic needle within said housing unit to prevent contact of said hypodermic needle with the operator of said device.

2. The device of claim 1 further comprising a plunger operatively engageable with and removable from the proximal end of said syringe, whereby when said plunger is pushed in the distal direction within said syringe and housing unit, liquid medicament is forced through said hypodermic needle, or when said plunger is pulled in the proximal direction within said syringe and housing unit, a body fluid sample is withdrawn through said hypodermic needle.

3. The device of claim 1 wherein said safety catch means comprises a safety catch having upwardly extending projection arms on the surface of said syringe, and having shafts connected to the ends of said arms and at the base of said safety catch, said housing further comprising guide means having sloping proximal terminii and protruding edges for engaging the shafts at the ends of said safety catch arms so as to press said arms inward as said syringe is pushed in the distal direction within said housing unit, and said terminii and protruding edges defining between them a notch, such that if said pushing force is released and said spring means extends and the syringe is moved proximally within said housing unit, said safety catch is moved into said notch such that the shafts of said safety catch abut against said terminii, and the syringe and hypodermic needle are thereby prevented from exiting proximally from the housing unit so as to expose the contaminated hypodermic needle.

4. The device of claim 1 wherein said safety catch means comprises tether means securing said syringe to said housing unit, said tether means being of a preselected length and attached to said housing unit and to the syringe whereby, if said pushing force applied to the proximal end of said syringe is released, and said spring means extends, the tether prevents said syringe and hypodermic needle from exiting proximally from the housing unit so as to expose the contaminated hypodermic needle.

5. The device of claim 1 wherein said locking means for selectively preventing relative movement between said syringe and hypodermic needle when the hypodermic needle is in use with the spring means compressed comprises:
   a compressable pad attached to the outer surface of said housing unit;
   a reversibly extensible pin attached to said pad, said pin for contacting the end of said syring opposite said needle for preventing movement of said syring and hypodermic needle proximally within said housing unit;
   an aperture located in the outer surface of said housing unit for introducing said pin into the interior of said housing unit; and
   spring means surrounding said pin and located within said pad, whereby when said pad is manually compressed said spring means compresses and said pin is extended through said aperture and into the interior of said housing unit, whereby said pin prevents proximal movement of said syringe within said housing unit.

6. The device of claim 5 wherein said syringe comprises a depression in the surface of said syringe for matingly receiving said pin when said pad is compressed, said depression located near the proximal end of said syringe, whereby when said pad is compressed said pin is inserted into said depression preventing proximal movement of said syringe within said housing unit.

7. The device of claim 1 further comprising additional locking means attached to the proximal end of said spring for retaining said hypodermic needle within said housing unit, said locking means comprising a block, a pocket formed within said block for receiving the base of said hypodermic needle, and said block having oppositely disposed, inwardly extending flanges for preventing exit of the base of the needle from the pocket.

8. The device of claim 1 wherein said syringe includes oppositely disposed upper and lower lips perpendicular to the circumference of the cylindrical body of said syringe, and said housing unit further comprises means for receiving said syringe and upper and lower lips.

9. The device of claim 8 wherein said means for receiving said syringe comprises oppositely disposed upper and lower channels located in the walls of said housing unit, said channels together defining a pathway for entry of said syringe into said housing unit, and said housing unit further including an upper strut located at the proximal end of said upper channel and perpendicular to the long axis of said upper channel, and said housing unit further including a ridge forming part of the circumference of said housing unit at the proximal end of said upper channel located across from said upper strut and having a flat surface positioned distally in said housing unit relative to said upper strut, and said housing unit including a lower strut located at the proximal end of said lower channel and perpendicular to the long axis of said lower channel and located on a diagonal relative to said upper strut, and said housing unit further including a ridge forming part of the circumference of said housing unit at the proximal end of said upper channel located across from said lower strut and having a flat surface positioned distally in said housing unit relative to said lower strut, whereby, when said syringe is first inserted into said housing unit, said upper and lower lips abut the flat surfaces of the ridges of said upper and lower notches whereby said syringe is advanced distally within said housing unit by rotating said syringe such that said upper and lower lips slide over said flat ridge surfaces and under the inner surfaces of said upper and lower struts, and by applying a pushing force to the proximal end of said syringe to compress said spring means to advance the syringe distally within the housing unit, and when said pushing force is released, said spring means extends and said syringe retracts proximally within said housing unit such that said upper and lower lips abut against the inner surfaces of said upper and lower struts so as to prevent unintended exit of said syringe from said housing unit, and said syringe may be removed from said housing unit by rotating said upper and lower lips out of contact with said upper and lower struts and pulling said syringe from the housing unit in the proximal direction.

10. The device of claim 1 or 9 wherein said syringe is a syringe for withdrawing fluid samples from a patient by vacuum.

11. The device of claim 1 further comprising cover means operably engageable with and removable from the outside of said housing unit for insulating and/or storing the contents of said syringe chamber.

12. The device of claim 11 further comprising means located between said housing unit and said cover means for contacting said syringe chamber to cool, heat, or insulate the contents of said syringe chamber.

13. The device of claim 1 or 9 wherein said housing unit is disposable.

* * * * *